US00PP21833P2

(12) United States Plant Patent
Horvath

(10) Patent No.: US PP21,833 P2
(45) Date of Patent: Mar. 29, 2011

(54) ***SEDUM* PLANT NAMED 'THUNDERCLOUD'**

(50) Latin Name: ***Sedum* hybrid**
Varietal Denomination: Thundercloud

(76) Inventor: Brent Horvath, Fontana, WI (US)

( * ) Notice: Subject to any disclaimer, the term of this patent is extended or adjusted under 35 U.S.C. 154(b) by 0 days.

(21) Appl. No.: 12/459,635

(22) Filed: Jul. 7, 2009

(51) Int. Cl.
*A01H 5/00* (2006.01)

(52) U.S. Cl. ..... Plt./479

(58) Field of Classification Search ..... Plt./263, Plt./479

See application file for complete search history.

*Primary Examiner*—Susan B McCormick Ewoldt

(57) ABSTRACT

A new, distinct *Sedum* plant as shown and described, characterized by pointed foliage, white flowers and a larger height compared to the seed parent.

2 Drawing Sheets

Latin name: *Sedum* hybrid.
Cultivar name: 'Thundercloud'.

BACKGROUND OF THE INVENTION

The present invention relates to a new and distinct hybrid of *Sedum* plant named 'Thundercloud' characterized by pointed or fingered foliage, white flowers and a larger height compared to the seed parent. The new *Sedum* was raised as a seedling from open pollinated seed sown as an unknown *Sedum tatranowii*, not patented, in Hebron, Ill. in 2005. The selection of the new plant was due to its' larger pointed foliage, larger white flowers and a taller height compared to the seed parent. Initial asexual reproduction has taken place at a nursery in Hebron, Ill. since 2006 by means of division, and vegetative cuttings. The new *Sedum* has shown to be stable and identical in reproduction to the parent after rooting over 1900 plants from 2006 to 2009.

SUMMARY OF THE INVENTION

The new *Sedum* plant named 'Thundercloud' characterized by pointed foliage, white flowers and a larger height compared to the seed parent have been observed to be unique and stable.

Plants of the new *Sedum* can be compared to plants of *Sedum spectabile* 'Stardust' not patented.

1. The new *Sedum* plant is a hybrid and does not produce seed while *Sedum spectabile* 'Stardust' is fertile and produces seed.
2. The new *Sedum* plant has a mature size measuring 25-30 cm high and 40-45 cm wide while *Sedum spectabile* 'Stardust' measures 45-55 cm high and 55-65 cm wide.
3. The new *Sedum* has white flowers with a hint of pink in them while *Sedum spectabile* 'Stardust' is entirely white.

Plants of the new *Sedum* can also be compared to the seed parent plant *Sedum tatranowii*, not patented.

1. The new plant is a hybrid and does not produce seed while the seed parent plant is fertile and produces viable seed.
2. The new *Sedum* has a mature size of 25-30 cm high and 40-45cm wide while the seed parent has a mature size of 12 cm high and 30 cm wide.

3. The new *Sedum* has larger foliage measuring on average up to 2 cm across by 5-6 cm long while the seed parent has foliage measuring 6 mm across by 2 cm long.
4. The new *Sedum* has a stem thickness of 5-8 mm while the seed parent has stem thickness of 2 mm.

DESCRIPTION OF PHOTOGRAPHS

Figure 1:
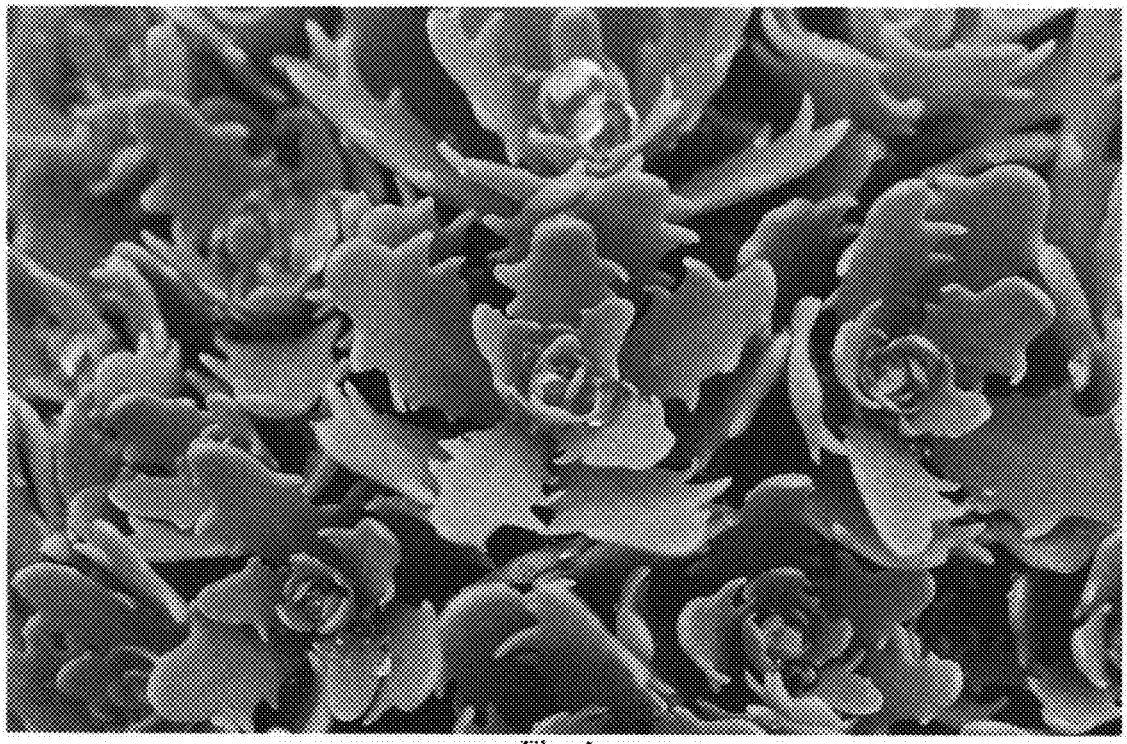
Figure 2:
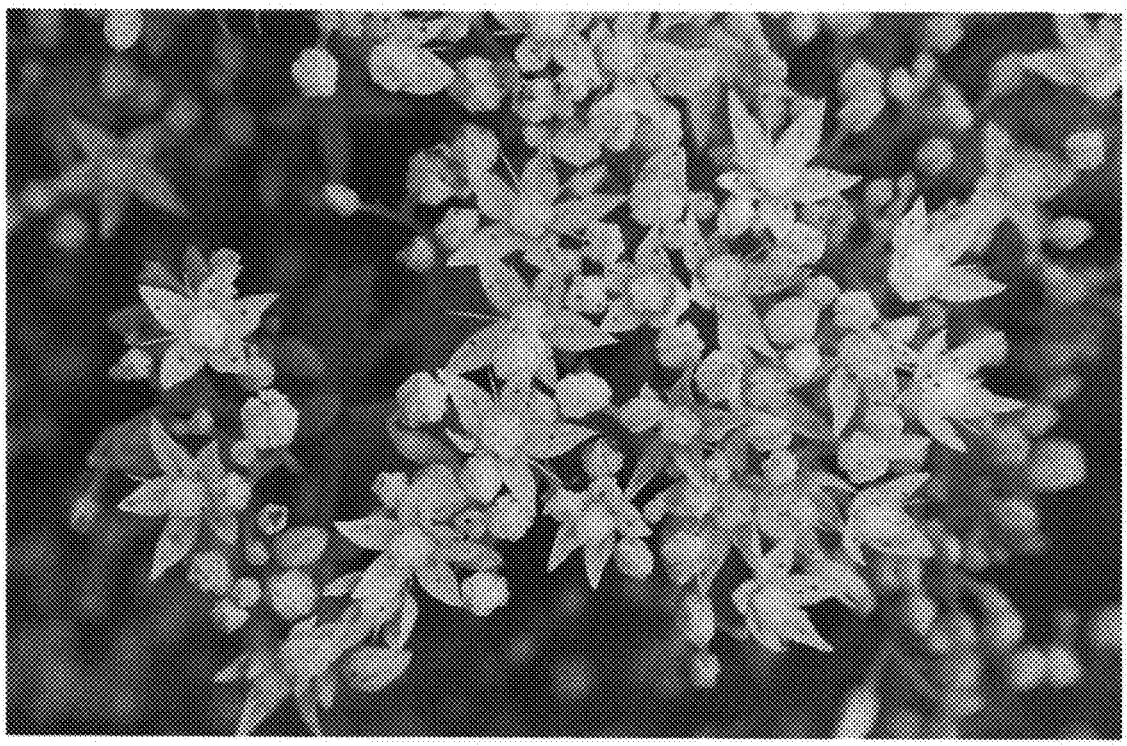
Figure 3:
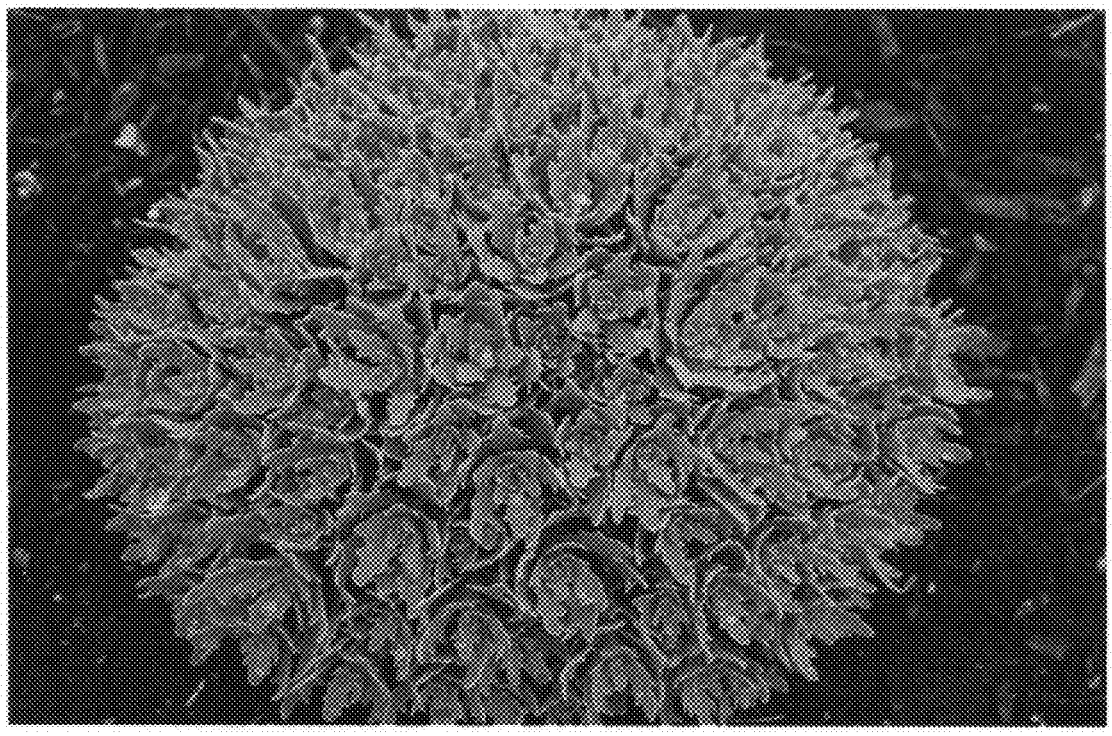

Plants pictured in the drawing were grown for three years.
FIG. 1. Close up of the foliage.
FIG. 2. Close up of the flower.
FIG. 3. A single plant in May.

DETAILED BOTANICAL DESCRIPTION

In the following description, color references are made to The Royal Horticultural Society Colour Chart (2001). Plants used for the description were grown for three years. Measurements and numerical values represent averages of typical plants.

Botanical classification: *Sedum* hybrid cultivar Thundercloud.

Parentage: Male or pollen unknown and female or seed an open pollinated, unknown *Sedum tatranowii*.

Propagation: Vegetative division and cutting propagation.

Plant description: Overall habit of the new *Sedum* is basal clumps, with upright stems topped by white flowers in August.

*Plant height.*—Average 25-30 cm.
*Plant width.*—40-45 cm.
*Stem color.*—144 A.
*Stem length.*—30 cm.
*Stem diameter.*—5-8 mm.

Foliage:

*Type.*—Deciduous.
*Shape.*—Obovate.
*Petiole.*—None.
*Length.*—5-6 cm.
*Width.*—2 cm.
*Thickness.*—1-2 mm.
*Margin.*—Coarsely and irregularly toothed.
*Texture.*—Smooth.
*Leaf arrangement.*—Alternate, crowded except at the base of the stems.

*Leaf venation pattern.*—None noticed.
*Leaf vein color.*—None noticed.
*Adaxial leaf description.*—Color is 137 B.
*Abaxial leaf description.*—Color is 137 D.
*Fall foliage color.*—None noticed.

Flower:

*Petal count.*—5.
*Petal shape.*—Lanceolate.
*Adaxial petal color.*—157 A.
*Abaxial petal color.*—154 C.
*Petal apex shape.*—Acuminate.
*Petal base.*—2-3 mm wide.
*Petal length.*—7 mm.
*Petal width.*—3 mm.
*Flower type.*—Panicle on basal flowering stems.
*Panicle color.*—As a whole the color is 155 A.
*Flower size.*—1 cm across, 5 mm tall.
*Flower number.*—Approximately 150-180 per stem.
*Bloom period and duration.*—Mid August to Mid September.
*Sepal size.*—1 mm across, 2 mm tall.
*Carpel color.*—N 155 C.
*Fertility.*—Sterile, 5 anthers no pollen, 5 stamens. Anthers can appear dark in color as they do in the FIG. 2. of the drawings.
*Blooming habit.*—Domed, terminal panicle on up to 35 cm stems.
*Scent.*—No scent noticed.
*Fruit.*—None.
*Disease resistance.*—Resistance to diseases common to *Sedum* has not been observed on plants grown under nursery conditions.

I claim:

1. A new, distinct *Sedum* plant as shown and described, characterized by pointed foliage, white flowers and a larger height compared to the seed parent.

* * * * *